US00PP33029P2

(12) United States Plant Patent
Van Langen

(10) Patent No.: US PP33,029 P2
(45) Date of Patent: May 4, 2021

(54) ECHEVERIA PLANT NAMED 'AMIECH1912'

(50) Latin Name: ***Echeveria* hybrid**
Varietal Denomination: AMIECH1912

(71) Applicant: NovoAmi B.V., Heerhugowaard (NL)

(72) Inventor: Gerard Van Langen, Heerhugowaard (NL)

(73) Assignee: NovoAmi B. V., Heerhugowaard (NL)

( * ) Notice: Subject to any disclaimer, the term of this patent is extended or adjusted under 35 U.S.C. 154(b) by 0 days.

(21) Appl. No.: 16/895,301

(22) Filed: Jun. 8, 2020

(51) Int. Cl.
*A01H 6/32* (2018.01)
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Samuel R. McCoy, Jr.

(57) ABSTRACT

A new and distinct *Echeveria* hybrid plant named 'AMIECH1912' which is characterized by broad obovate to spatulate foliage held somewhat loosely in a basal rosette, moderately glossy juvenile foliage, vibrant dark red juvenile foliage that is margined pink, slightly glossy mature foliage, very dark purple mature foliage that is narrowly margined pink, and the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* hybrid disclosed herein has been given the variety denomination 'AMIECH1912'.

CROSS REFERENCE TO RELATED APPLICATIONS

This application claims priority to the Community Plant Variety Rights application number 2019/3324, filed Dec. 6, 2019, which is herein incorporated by reference.

BACKGROUND OF THE INVENTION

Parentage: 'AMIECH1912' is a naturally-occurring, spontaneous whole-plant mutation of *Echeveria* hybrid 'AMIECH1604' (U.S. Plant Pat. No. 29,312) which was discovered by the inventor in the summer of 2018 at a commercial greenhouse in Heerhugowaard, the Netherlands. The mutation was noted for its very dark purple foliage.

Asexual Reproduction: Asexual reproduction of the new cultivar 'AMIECH1912', by way of rooting leaf cuttings, was first initiated in the winter of 2018 at the inventor's commercial greenhouse in Heerhugowaard, the Netherlands. Through two subsequent generations, the unique features of this cultivar have proven to be stable and true to type.

SUMMARY OF THE INVENTION

The cultivar 'AMIECH1912' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH1912'. These characteristics in combination distinguish 'AMIECH1912' as a new and distinct *Echeveria* hybrid cultivar:

1. 'AMIECH1912' exhibits a flattened to flattened globular plant profile with foliage held somewhat loosely in a basal rosette which eventually forms a short, unbranched stem with age; and
2. 'AMIECH1912' exhibits slightly concave, broad obovate to spatulate foliage with a bluntly apiculate apex; and
3. 'AMIECH1912' exhibits moderately glossy, lightly glaucescent juvenile foliage; and
4. 'AMIECH1912' exhibits greyed-purple juvenile foliage, generally appearing as a vibrant dark red general coloration with pink margins; and
5. 'AMIECH1912' exhibits slightly glossy, lightly glaucescent mature foliage; and
6. 'AMIECH1912' exhibits mature foliage that is colored in between greyed-purple and brown, generally appearing as very dark purple to nearly black; and
7. 'AMIECH1912' exhibits mature foliage that is narrowly margined pink.

BOTANICAL DESCRIPTION OF THE PLANT

Figure 1:
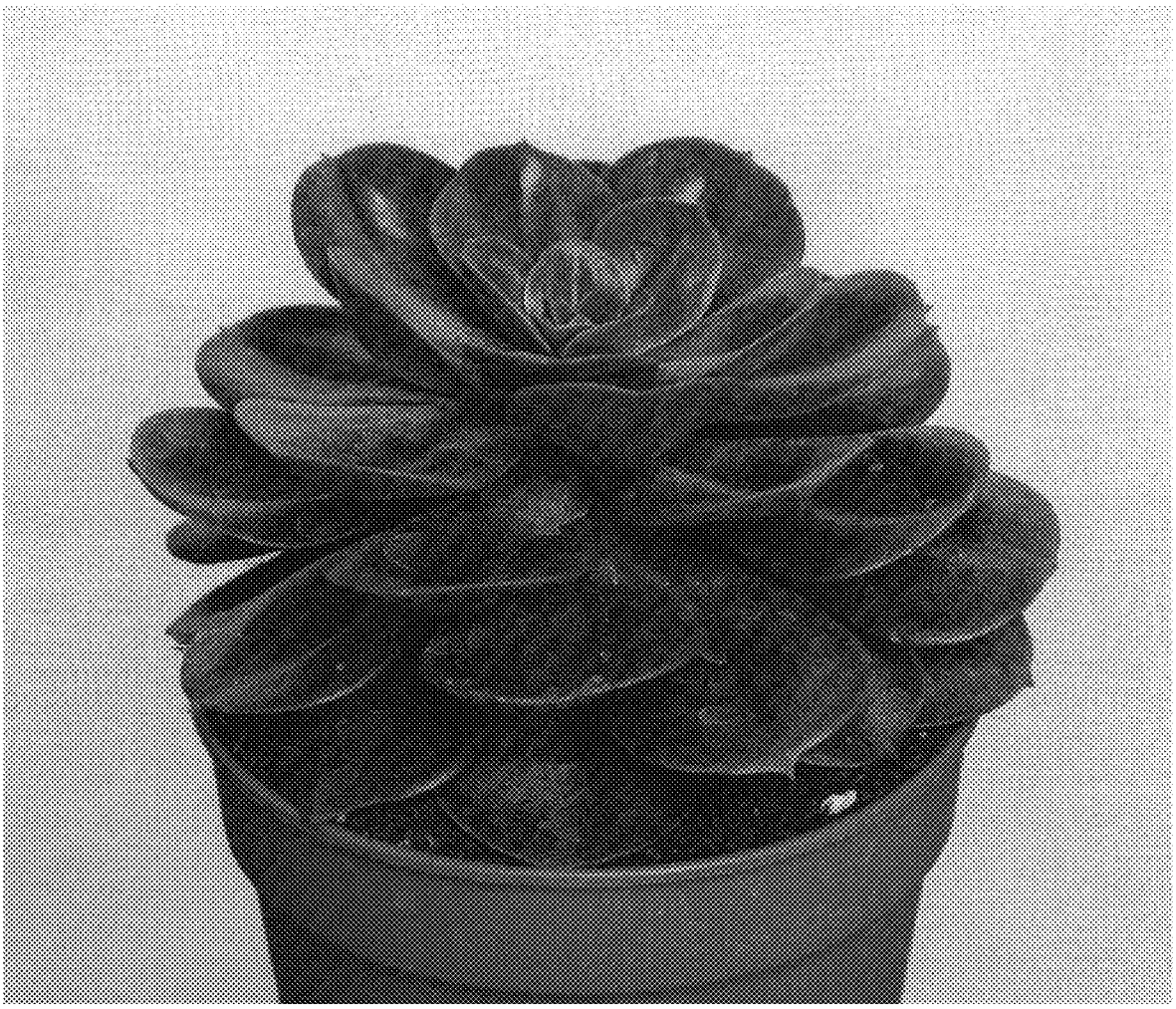
FIG. 1 illustrates, as nearly true as it is reasonably possible to make the same in color photographs of this type, an exemplary plant of 'AMIECH1912' grown in a commercial greenhouse in Heerhugowaard, the Netherlands. This plant is approximately 8 months old, shown planted in an 12 cm container.
Figure 2:
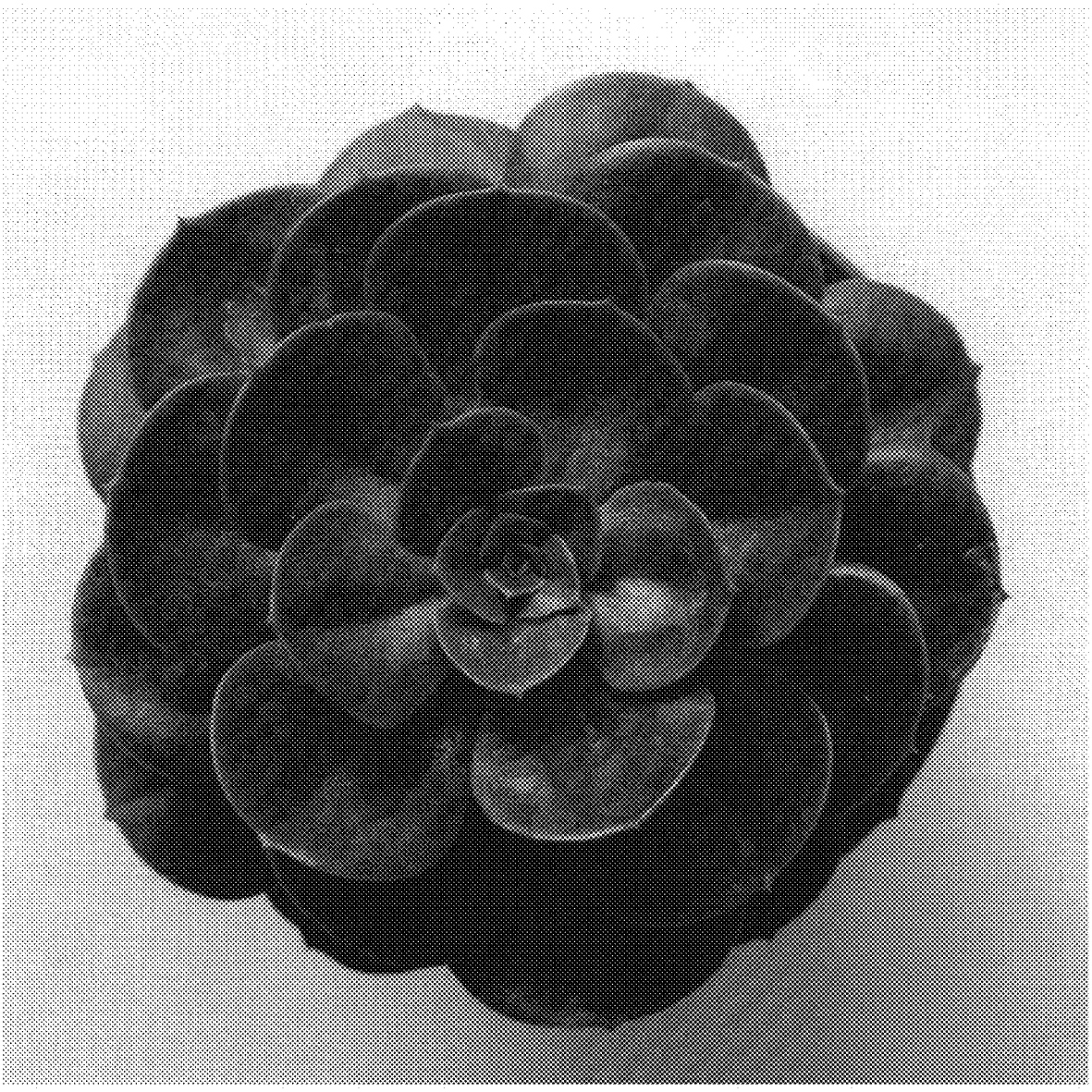
FIG. 2 illustrates, as nearly true as it is reasonably possible to make the same in color photographs of this type, the typical foliage arrangement of 'AMIECH1912.
Figure 3:
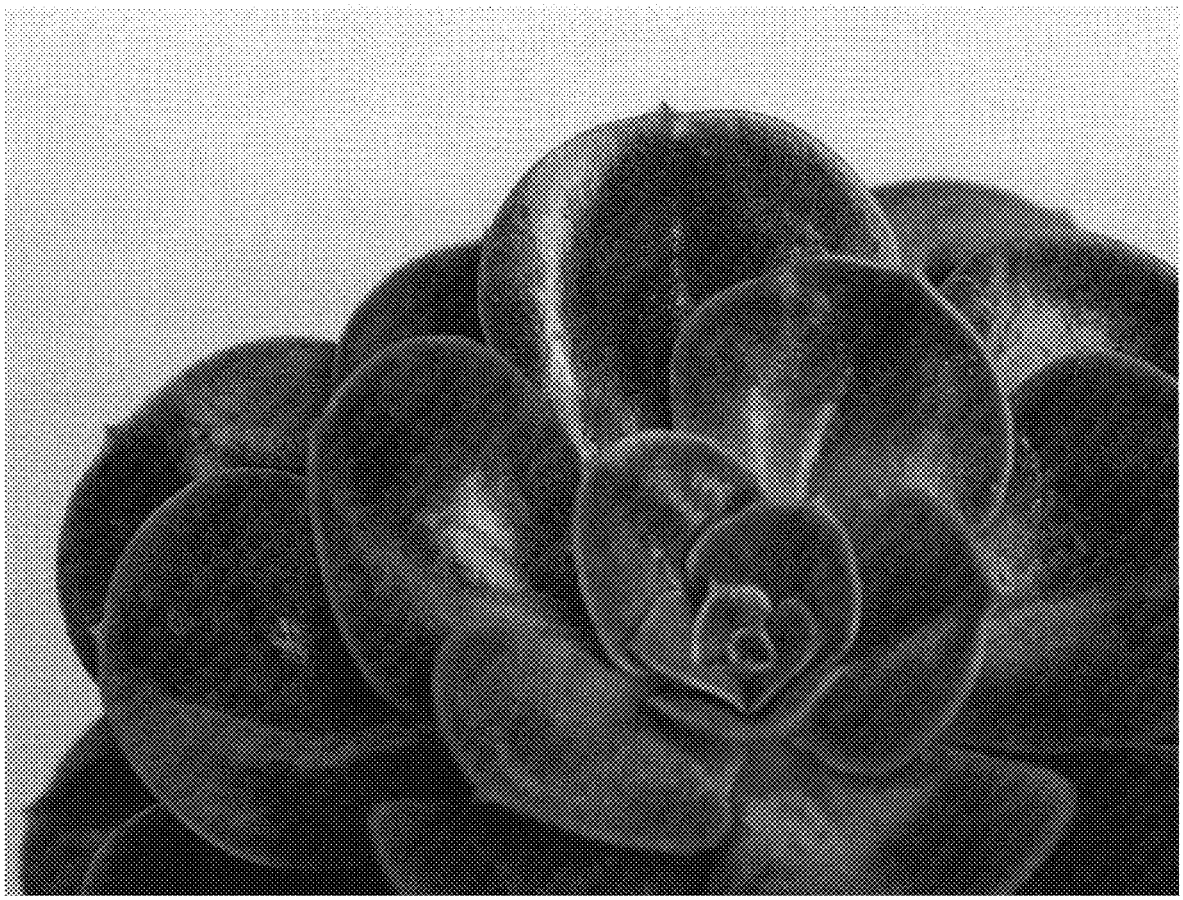
FIG. 3 illustrates, as nearly true as it is reasonably possible to make the same in color photographs of this type, the adaxial surface of the mature foliage 'AMIECH1912'.
Figure 4:
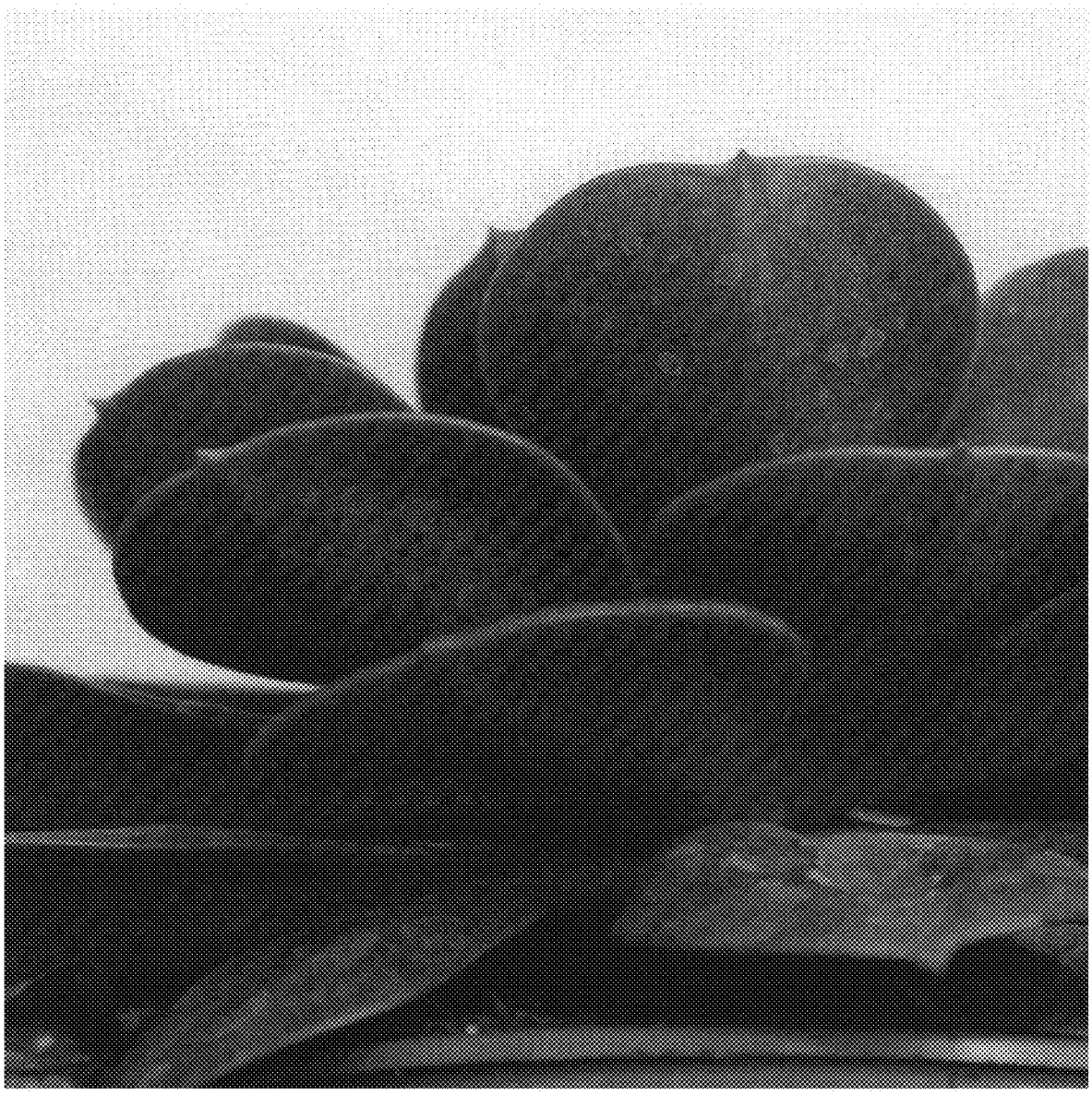
FIG. 4 illustrates, as nearly true as it is reasonably possible to make the same in color photographs of this type, the abaxial surface of the mature foliage 'AMIECH1912'.

The following observations and measurements made in January of 2020 describe averages from a sample set of six specimens of 8 months old 'AMIECH1912' plants grown in 12 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH1912' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'AMIECH1912' and comparisons with the parent plant and closest known comparator are provided below.

Plant description:

*Growth habit*.—Succulent perennial with foliage growing in a basal rosette, eventually forming a short, unbranched stem with age.

*Plant shape*.—Flattened to flattened globular.

*Height from soil level to top of foliar plane*.—7.6 cm.

*Plant spread*.—Average of 13.9 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in a 7 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a basal rosette, eventually forming a short, unbranched stem with age; no lateral branching.

*Quantity of main stems*.—1.

*Main stem dimensions*.—4.5 cm long and 1.1 cm in diameter.

*Internode length*.—0.1 cm.

*Cross section*.—Rounded.

*Aspect*.—Nearly vertical.

*Strength*.—Strong.

*Texture and luster*.—Glabrous, glaucous, and moderately glossy.

*Color, when developing*.—Nearest to in between purple and greyed-purple, nearest to RHS 75D.

*Color of mature stem*.—Greyed-purple, nearest to RHS 186B.

*Color at internodes*.—Greyed-purple, nearest to RHS 186B.

Foliage:

*Arrangement*.—Rosette.

*Division*.—Simple.

*Attachment*.—Sessile.

*Quantity*.—Approximately 39 leaves per rosette.

*Shape*.—Broad obovate to spatulate.

*Dimensions*.—6.7 cm long, 4.2 cm wide, and 0.5 cm thick, on average.

*Aspect*.—Slightly to moderately concave.

*Attitude*.—Juvenile foliage at the center of the rosette is held upward and outward; foliage becomes progressively more relaxed towards the outer whorls of mature foliage.

*Apex*.—Bluntly apiculate.

*Base*.—Long cuneate.

*Margin*.—Entire; not undulate.

*Pubescence, texture and luster of the adaxial surface*.—Glabrous, smooth, and lightly glaucous. The thin layer of epicuticular wax is color the same as the underlying foliage.

*Pubescence, texture and luster of the abaxial surface*.—Glabrous, smooth, and lightly glaucous. The thin layer of epicuticular wax is color the same as the underlying foliage.

*Luster of the adaxial surface*.—Juvenile foliage is moderately glossy; mature foliage is slightly glossy.

*Luster of the abaxial surface*.—Juvenile foliage is moderately glossy; mature foliage is slightly glossy.

*Color*.—Juvenile foliage, adaxial surface — Greyed-purple, nearest to RHS 187A, and fading lighter towards the base, nearest to RHS 184D; margined greyed-purple, nearest to RHS 185B. Juvenile foliage, abaxial surface — Greyed-purple, nearest to RHS 187B, and fading lighter towards the base, nearest to RHS 184D; margined greyed-purple, nearest to RHS 185B. Mature foliage, adaxial surface — Nearest to in between greyed-purple and brown, RHS N186C and 200A; fading to greyed-red towards the base, nearest to RHS 182C, and suffused with greyed-orange, nearest to RHS 177B; margined greyed-red, nearest to RHS 178B. Mature foliage, abaxial surface — Brown, nearest to RHS 200C, and lightly suffused with greyed-purple, nearest to RHS N186C; fading to greyed-red towards the base, nearest to RHS 181C, and suffused with greyed-orange, nearest to RHS 177B; margined greyed-red, nearest to RHS 178B. Venation, adaxial surface — Only the main vein of the abaxial surface is visible. Venation, abaxial surface — Only the main vein is visible;

colored greyed-purple, nearest to a mixture of RHS 183A and 183B.

*Petiole*.—No petiole; leaves are sessile.

Inflorescence: No flowering has been observed to date.

Comparisons With the Parent Plant and Closest Known Comparator

Plants of the new cultivar 'AMIECH1912' differ from the parent, *Echeveria* hybrid 'AMIECH1604' (U.S. Plant Pat. No. 29,312), in the following characteristics described in Table 1 below.

TABLE 1

| Characteristic | 'AMIECH1912' | 'AMIECH1604' |
|---|---|---|
| Abundance of foliage. | More abundant than 'AMIECH1604'. | Less abundant than 'AMIECH1912'. |
| Foliage luster. | Moderately glossy juvenile foliage; slightly glossy mature foliage. | All foliage is matte. |
| General coloration of the juvenile foliage. | Greyed-purple, generally appearing as a vibrant dark red by comparison to 'AMIECH1604'. | Greyed-purple, generally appearing as a softer, lighter red by comparison to 'AMIECH1912'. |
| General coloration of the mature foliage. | In between greyed-purple and brown, generally appearing as very dark purple to nearly black. | A mixture of greyed-green and yellow green, suffused with greyed-red. |

Comparisons With the Closest Known Comparator

Plants of the new cultivar 'AMIECH1912' differ from the closest known commercial comparator, *Echeveria* hybrid 'Purple Pearl' (Community Plant Variety Rights application number 30403), in the following characteristics described in Table 2 below.

TABLE 2

| Characteristic | 'AMIECH1912' | 'Purple Pearl' |
|---|---|---|
| Foliage glaucescence. | Lightly glaucescent. | Moderately to heavily glaucescent. |
| Foliage luster. | Moderately glossy juvenile foliage; slightly glossy mature foliage. | All foliage is matte. |
| General coloration of the juvenile foliage. | Greyed-purple, generally appearing as a vibrant dark red by comparison to 'AMIECH1604'. | Light purple, suffused with pink. |
| General coloration of the mature foliage. | In between greyed-purple and brown, generally appearing as very dark purple to nearly black. | Olive green, suffused with light purple. |

That which is claimed is:

1. A new and distinct variety of *Echeveria* hybrid plant named 'AMIECH1912', substantially as described and illustrated herein.

* * * * *